United States Patent
Weg

[11] Patent Number: 5,989,582
[45] Date of Patent: Nov. 23, 1999

[54] ADMINISTRATION OF KETAMINE FOR DETOXIFICATION AND TO TREAT SUBSTANCE ADDICTION, AND COMPOSITIONS THEREFOR

[76] Inventor: Stuart L. Weg, 498 Island Way, Franklin Lakes, N.J. 07417

[21] Appl. No.: 08/894,845

[22] PCT Filed: Feb. 14, 1996

[86] PCT No.: PCT/US96/02047

§ 371 Date: Aug. 14, 1997

§ 102(e) Date: Aug. 14, 1997

[87] PCT Pub. No.: WO96/25925

PCT Pub. Date: Aug. 29, 1996

Related U.S. Application Data

[63] Continuation of application No. 08/477,365, Jun. 7, 1995, Pat. No. 5,679,714, which is a continuation-in-part of application No. 08/201,756, Feb. 25, 1994, Pat. No. 5,543,434.

[51] Int. Cl.$^6$ .............................. A61F 13/02; A61K 47/18
[52] U.S. Cl. ........................... 424/434; 424/430; 424/435; 424/439; 424/443
[58] Field of Search ..................................... 424/430, 434, 424/435, 443, 439

[56] References Cited

U.S. PATENT DOCUMENTS

| | | |
|---|---|---|
| 4,334,526 | 6/1982 | Hamacher . |
| 4,671,953 | 6/1987 | Stanley et al. . |
| 5,112,804 | 5/1992 | Kowarski . |
| 5,132,114 | 7/1992 | Stanley et al. . |
| 5,679,714 | 10/1997 | Weg ....................................... 514/647 |

FOREIGN PATENT DOCUMENTS

| | | |
|---|---|---|
| 1322958 | 10/1988 | Canada . |
| WO 91/03236 | 3/1991 | WIPO . |
| WO 93/15737 | 8/1993 | WIPO . |
| WO 95/22965 | 8/1995 | WIPO . |

OTHER PUBLICATIONS

Trujillo and Akil. 1994. Brain Res. 633:178–88.
Abram. 1993. Reg. Anesth. 18 (suppl):406–13.
Louon et al. 1993. Br. J. Opthalmol. 77:529–30.
Jansen. 1993. Brit. Med. J. 306:601–02.
Stannard and Porter. 1993. Pain 54:227–30.
Weksler et al. 1993. Can. J. Anaesthia 40:119–21.
Adams and Hempelmann. 1990. Anaesthesist 39:71–76. (English abs.).
Oshima et al. 1990. Can. J. Anaesth. 37:385–92.
Reich and Silvay. 1989. Can. J. Anaesth. 36:186–97.
Sadove et al. 1971. Anesth. Analg. 50:452–57.
Bovill and Dundee. 1971. Br. J. Anaesth. 43:496–94.
Domino et al. 1965. Clin. Pharmacol. Ther. 6:279–91.
Aldrete et al. (1988) Acta Anaesthesiol. Belg. 39 (No.3, Sup.2):95–6.
Weksler et al. (1993) Can. J. Anaesth. 40:119–21.
Adams et al. (1990) Anaesthesist 39:71–6.
Raju, V.K. (1990) West. J. Med. 153:311–2.
Anderson, C.T.M. (1980) J. Pediatr. Ophthalmol. Strabismus. 17:292–6.
Khanna et al. (1992) Pharmcol. Biochem. Behav. 42:347–50.
Khanna et al. (1993) Soc. Neurosci. Abstr. 19:1456 (Abst. # 595.5).
Raju, V.K. (1980) J. Pediatr. Ophthalmol. 17:292–6.

*Primary Examiner*—Carlos Azpuru
*Attorney, Agent, or Firm*—Darby & Darby

[57] ABSTRACT

A method to facilitate detoxification and treat substance addiction by administration of ketamine and a benzodiazepine. A preferred dosage range of ketamine is about 0.01 mg/kg of body weight to about 1 mg/kg. Pharmaceutical compositions comprising this dosage range of ketamine in a gum or candy are also provided. In a specific example, a dedicated smoker was able to reduce her craving from three packs of cigarettes a day.

14 Claims, No Drawings

ADMINISTRATION OF KETAMINE FOR DETOXIFICATION AND TO TREAT SUBSTANCE ADDICTION, AND COMPOSITIONS THEREFOR

This application is a Section 371 national application of PCT/US96/02047, filed Feb. 14, 1996, which is a continuation of application Ser. No. 08/477,365, filed Jun. 7, 1995, now U.S. Pat. No. 5,679,714, which is a continuation-in-part of application Ser. No. 08/201,756, filed Feb. 25, 1994, now U.S. Pat. No. 5,543,434.

FIELD OF THE INVENTION

The present invention relates to methods to assist detoxification and treatment for addictive diseases, particularly smoking.

BACKGROUND OF THE INVENTION

Ketamine ((2-(2-chlorophenyl)-2-(methylamino)-cyclohexanone) is a general anesthetic used by anesthesiologists, veterinarians, and researchers. Nasal administration of ketamine, in one instance with midazolam, to achieve sedation for an ophthalmic procedure, and prior to elective surgery in healthy children has been reported (Louon et al., 1993, Br. J. Ophthalmol. 77: 529–530; Weksler et al., 1993, Can. J. Anaesthesia 40: 119–121). Usually, ketamine is administered intramuscularly (i.m.) or intravenously (i.v.) for induction of anesthesia.

Ketamine has also been known to have analgesic properties (Domino et al., 1965, Clin. Pharmacol. Ther. 6: 279); analgesia can be achieved with subanesthetic doses of ketamine (Bovill, 1971, Br. J. Anaesth. 43: 496; Sadove et al., 1971, Anesth. Analg. 50: 452–457). The drug is administered by various routes, including i.v., i.m., caudal, intrathecal, and subcutaneous (s.c.). Subcutaneous administration of ketamine has been used to treat pain following surgery and associated with terminal cancer (see, e.g., Oshima et al., 1990, Can. J. Anaesth. 37: 385–386). Ketamine hydrochloride administered via a subcutaneous cannula was reported to successfully treat phantom limb pain (Stannard and Porter, 1993, Pain 54: 227–230).

Detoxification and treatment of addictive diseases generally involves a complex and poorly understood interplay between the psychological and physiological components. Seven withdrawal symptoms can accompany detoxification from substances such as alcohol, narcotics, depressants, and stimulants. While marked by significantly less severe physical symptoms, the withdrawal symptoms associated with detoxification from smoking may include nervousness, shakiness, difficulty concentrating, impatience, and ill tempered behavior. Furthermore, detoxification is only an acute component of the treatment of addictive disease. Long term treatment, to be successful, must provide strong physical and psychological reinforcements to avoid the addition.

Thus, an area of grave concern for medicine is detoxification and withdrawal from dependence on addictive substances, including narcotics, cocaine, alcohol, and tobacco (both nicotine and smoking itself). In particular, medicine provides no satisfactory relief for withdrawal from smoking or from nicotine addiction. While the general perception holds that addiction to tobacco is the least profound of these addictions, from a public health perspective, it may be the most important. Furthermore, the current supports for treatment of smoking or nicotine addiction, such as the nicotine transdermal patch or nicotine gum, treat the addiction with an addictive substance delivered by tobacco use. Such treatment is logically impossible: it reinforces the very behavior to be eliminated. No adequate substitute, capable of reinforcing the absence of tobacco ingestion, is presently available.

Thus, there is still a critical need in the art for an agent that can assist in detoxification and withdrawal from addiction to substances, particularly smoking.

The citation or identification of any reference in this application shall not be construed as an admission that such reference is available as prior art to the present invention.

SUMMARY OF THE INVENTION

The present invention is broadly directed to a method for assisting detoxification and treatment of substance addiction in a subject comprising administering a dose of ketamine effective to assist in detoxification and treatment of the addiction. In a preferred aspect, ketamine is administered transmucosally, more preferably, nasally. In a further embodiment, the present invention provides for pulmonary administration of ketamine by inhalation. Where a patient's condition prevents nasal administration of ketamine, ocular administration, using, e.g., ketamine drops, can be substituted. In addition to transmucosal administration of ketamine, e.g., nasal, transbuccal, sublingual, vaginal, and rectal, the invention contemplates oral administration (via the gastrointestinal tract, rather this oral-pharyngeal mucosa), and parenteral administration, e.g., intravenous, intraarterial, intraperitoneal, intradermal, intramuscular, intraventricular, or subcutaneous.

It has also been found that administration of an analgesic dose of ketamine advantageously provides a powerful reinforcement for not engaging in the addictive behavior, e.g., smoking or taking drugs. The invention allows for patient self administration of the drug, which facilitates detoxification and treatment for addiction on an outpatient basis. Ketamine administration in nasal sprays and inhalers is generally socially acceptable.

In a preferred embodiment, the invention provides a method and device for detoxification and treating addiction to tobacco, i.e., smoking.

A further advantage of the invention is that it avoids the administration of the addictive substance, particularly nicotine, for the treatment of the addiction.

Yet a further advantage of the invention is that ketamine is an inexpensive, readily available drug, with minor adverse side effects. Thus, the invention contemplates additional savings to the overburdened health care system.

Nasal administration of ketamine is rapid, allowing for fast action of the drug, and easily accomplished by a non-medically trained patient.

In one aspect, the addiction treating dose of ketamine is approximately 0.01 to approximately 1 mg/kg of body weight. In a more preferred aspect, the dose of ketamine is approximately 0.05 to approximately 0.7 mg/kg of body weight. In another embodiment, the total dose of ketamine per nasal administration ranges from about 1 to about 30 mg.

In a particular aspect, nasal administration of ketamine can be a supplemental therapy in a pain management regimen that includes administration of one or more of narcotics, analgesics, and sedatives, e.g., as described above.

The present invention further contemplates administering a dose of a benzodiazepine effective to inhibit dysphoria that can be associated with administration of high doses of ketamine. In a preferred aspect, the benzodiazepine is administered nasally with the ketamine. The sedatory effects of the benzodiazepine may also reduce some of the agitation and nervousness that accompany detoxification (withdrawal).

It should be noted that a further advantage of the instant invention is that it avoids dosing a patient with dysphoric or hallucinogenic amounts of ketamine by providing an analgesic dose, which is well below the level associated with dysphoria or hallucination.

Accordingly, in a preferred embodiment, the invention provides a device for patient self-administration of ketamine. In its broadest aspect, the device of the invention comprises a nasal inhaler containing an aerosol formulation of ketamine and a pharmaceutically acceptable dispersant, wherein the device is metered to disperse an amount of the aerosol formulation that contains a dose of ketamine effective to alleviate pain or assist in detoxification and treatment of addiction. The dispersant may be a surfactant, such as, but not limited to, polyoxyethylene fatty acid esters, polyoxyethylene fatty acid alcohols, and polyoxyethylene sorbitan fatty acid esters.

In a specific embodiment, particularly for treatment of addiction, the device provides a metered dose of ketamine and includes a dose limiting mechanism that limits the number of doses, and preferably includes a "lock-out" time before another dose can be administered.

In further embodiments, the aerosol formulation further comprises a benzodiazepine in a concentration such that the metered amount of the aerosol formulation dispersed by the device contains a dose of the benzodiazepine effective to inhibit dysphoria, or a narcotic in a concentration such that the metered amount of the aerosol formulation dispersed by the device contains a dose of the narcotic effective to alleviate pain. The present invention further contemplates including both a benzodiazepine and a narcotic in the aerosol formulation.

Thus, it is an object of the invention to provide for self administration of a safe, non-narcotic drug for assisting in detoxification and treatment of addiction.

It is a further object of the present invention to provide for administration of a drug in a controlled amount for assisting in detoxification and treatment of addiction.

Yet a further object of the invention is to provide a device that can be used outside a hospital or medical office by non-medical personnel for nasal self administration of ketamine.

These and other objects of the present invention will become more readily apparent by reference to the following detailed description.

DETAILED DESCRIPTION OF THE INVENTION

One aspect of the invention provides for nasal administration of ketamine to facilitate detoxification and to assist in the treatment of substance addiction, particularly smoking. In a more preferred aspect, the invention provides a method and device for patient self administration of ketamine for detoxification and treatment of substance addiction.

In yet another related embodiment, administration of ketamine can be used in the treatment of acute nausea associated with withdrawal. Transmucosal, especially nasal or rectal, ketamine is particularly attractive for this condition, as nausea precludes the use of oral medications. In particular, ketamine can alleviate pain that may be causing the nausea, and can alleviate the abdominal pain that frequently accompanies severe nausea.

In yet a further related embodiment, administration of ketamine can be used to treat acute agitation, for example, agitation exhibited by an alcohol or drug intoxicated individual, e.g., when such a person is placed under arrest by the police.

In a preferred aspect, administration of ketamine is a powerful and effective adjunct to smoking cessation. In a more preferred aspect, the invention provides for transmucosal administration, preferably nasal, but also including fecal, sublingual, or rectal (via a suppository), to mention a few preferred routes. A number of individuals, some of whom were strongly addicted to smoking, have been able to break the addiction through nasal administration of ketamine rather than smoking a cigarette when the urge to smoke strikes.

The invention is further based on the unexpected discovery that nasal administration of ketamine is a powerful reinforcement for withdrawal from and avoiding addictive substances, such as smoking tobacco, narcotics, and others. In particular, nasal administration of ketamine has allowed strongly addicted smokers to avoid cigarettes immediately. Although not intending to be bound by any particular theory for the mechanism by which ketamine aids in the treatment of substance addiction, it is believed that the anesthetic properties compensate for the euphoric effects of addictive substances. For example, during smoking endorphins are secreted in response to carbon monoxide (CO) induced hypoxia, and these endorphins provide a powerful reinforcement to the smoking behavior. Endorphins are opioid peptides that bind to the same receptors as opioids. As noted above, ketamine is capable of alleviating intractable pain that ordinarily is treated with opioids. Thus, the observation that ketamine administration is highly effective in treating addiction to smoking is consistent with ketamine's ability to supplement or surpass the opioids in treating pain.

As pointed out in International Patent Application No. PCT/US95/02418, filed Feb. 24, 1995, it has been found that dozens of patients suffering from intractable pain, migraine headache, chronic fatigue syndrome, and other pain-associated afflictions, have benefitted from nasal administration of ketamine, and devices modified for nasal administration of ketamine. Moreover, those of the patients who smoke have found that nasal ketamine strongly inhibits the urge to smoke.

Accordingly, in a preferred aspect the present invention is directed to methods for assisting in detoxification and treatment of substance addiction, on an outpatient basis by nasal or rectal administration of ketamine, and to devices usable by non-medical personnel for nasal or rectal self-administration of ketamine.

Ketamine will preferably be prepared in a formulation or pharmaceutical composition appropriate for transmucosal, e.g, nasal, buccal, sublingual, or rectal administration. Suitable formulations are discussed in detail, infra. In a further embodiment, ketamine can be formulated with a mucosal penetration enhancer to facilitate transmucosal delivery of the drug. The formulation can also be prepared with pH optimized for solubility, drug stability, absorption through mucosa, and other considerations.

The invention provides for administration of a therapeutically effective dose of ketamine, i.e., a dose effective facilitate detoxification and assist in treatment of substance addiction. The actual dose will vary, depending on the body weight of the patient, the severity of the or substance addiction, the route of administration, the nature of medications administered concurrently, the number of doses to be administered per day, and other factors generally considered by the ordinary skilled physician in the administration of drugs. In a specific embodiment, the amount of ketamine administered is about 10% to about 20% of the amount used to induce anesthesia. In another specific embodiment, the dose of ketamine is about 0.01 mg per kg of body weight (0.01 mg/kg) to about 1 mg/kg; preferably about 0.05 mg/kg to about 0.7 mg/kg. In yet another embodiment, the total dose ranges from about 1 mg to about 30 mg. Preferably, the effective dose is titrated under the supervision of a physician or medical care provider, so that the optimum dose for the particular application is accurately determined. Thus, the present invention provides a dose suited to each individual patient.

Once the dosage range for transmucosal administration is established, a further advantage of the invention is that the patient can administer ketamine on an as-needed, dose-to-effect basis. Thus, the frequency of administration is under control of the patient. However, the relatively low dose with each administration will reduce the possibilities for abuse.

More importantly, in the preferred aspect for transmucosal administration, a patient can control administration of the ketamine, because administration provides for precise control over the dosage and effect of the drug used to offset changes in activity and pain levels throughout a day. Transmucosal administration of ketamine optimally provides for dose-to-effect administration of the drug.

Thus, according to the invention, the patient can safely administer an amount of drug effective for assisting in withdrawal and treatment of substance addiction by controlling the amount and frequency of administration of a formulation according to the invention. Safe patient regulated control of medicine for treating addition is an important advantage because addiction is such a subjective condition. The advantage is two-fold here, as the patient can effectively eliminate or greatly reduce craving, and the power to reduce the craving will have significant psychological benefits. A positive psychological attitude can significantly improve the course and outcome of a treatment regimen, as well as making the entire process more bearable to the patient.

Similarly, ketamine, which is not itself addictive, is a powerful reinforcement for avoiding addictive substances. In order to avoid abuse by the addictive personality, ketamine for administration to assist in detoxification or treatment of substance addiction can be provided in a metered dose device, e.g., a device containing a dose limiting mechanism. The dose limiting mechanism can provide a limited number of dosages of ketamine, with a "lock-out" time between doses to avoid too frequent administration.

Various terms are used throughout the specification, which are defined herein:

The term "mucosal" refers to a tissue comprising a mucous membranes, such as the nasal mucosa, pulmonary mucosa, oral mucosa (sublingual, buccal, pharyngeal), rectal (via a suppository).

The term "transmucosal administration" in all its grammatical forms refers to administration of a drug through the mucous membrane to the bloodstream for systemic delivery of the drug. The advantages transmucosal administration for drug delivery are that it does not require injection using a syringe and needle, it avoids necrosis that can accompany i.m. administration of drugs, it avoids the need to constantly such on a lollipop, and trans-mucosal administration of a drug is highly amenable to self administration.

The present invention further contemplates pulmonary administration through an inhaler in a particular aspect.

The term "mucosal penetration enhancer" refers to a reagent that increases the rate or facility of transmucosal penetration of ketamine, such as but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol. Suitable penetration enhancers also include glycyrrhetinic acid (U.S. Pat. No. 5,112,804 to Kowarski) and polysorbate-80, the latter preferably in combination with an non-ionic surfactant such as nonoxynol-9, laureth-9, poloxamer-124, octoxynol-9, or lauramide-DEA (European Patent EP 0 242 643 B1 by Stoltz).

A "therapeutically effective amount" of a drug is an amount sufficient to demonstrate a desired activity of the drug. According to the instant invention, in one embodiment a therapeutically effective amount of ketamine facilitates detoxification of a subject from an addictive substance. In yet another embodiment, a therapeutically effective amount is an amount facilitates treatment of a substance addiction, i.e., an amount effective as a reinforcement for avoiding the addictive substance or addictive behavior.

The term "substance addiction" refers to an addiction or habit associated with a particular addictive substance. The term "addictive substance" refers to a drug or agent capable of causing an addiction, including but not limited to narcotics, depressants, amphetamines, opioid analgesics, cocaine, marijuana, tobacco (particularly smoking, both for the mild hypoxic euphoria it causes, and the nicotine contained therein), and alcohol.

A subject in whom administration of ketamine is an effective therapeutic regiment for treatment of substance addiction is preferably a human, but can be any animal. Thus, as can be readily appreciated by one of ordinary skill in the art, the methods and devices of the present invention are particularly suited to administration of ketamine to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

The invention will now be described in greater detail, with particular reference to transmucosal, such as nasal, pulmonary, rectal, transbuccal, and sublingual administration of ketamine and additional therapeutically active drugs or agents with which ketamine can be administered.

Nasal/Pulmonary Administration

The present invention contemplates formulations comprising ketamine for use in a wide variety of devices that are designed for the delivery of pharmaceutical compositions and therapeutic formulations to the respiratory tract, preferably the nasal passages. The preferred route of administration of the present invention is in an aerosol spray for nasal inhalation. Ketamine, preferably combined with a dispersing agent, or dispersant, can be administered in an aerosol formulation as a dry powder or in a solution or suspension with a diluent.

As used herein, the term "aerosol" refers to suspension in the air. In particular, aerosol refers to the particlization or atomization of a formulation of the invention and its suspension in the air. According to the present invention, an aerosol formulation is a formulation comprising ketamine for nasal inhalation or pulmonary administration.

As used herein, the term "inhaler" refers both to devices for nasal and pulmonary administration of a drug, e.g., in solution, powder and the like. For example, the term "inhaler" is intended to encompass a propellant driven inhaler, such as is used for to administer antihistamine for acute asthma attacks, and plastic spray bottles, such as are used to administer decongestants.

As used herein, the term "dispersant" refers to a agent that assists aerosolization of the ketamine or absorption of the ketamine in mucosal tissue, or both. In a specific aspect, the dispersant can be a mucosal penetration enhancer. Preferably, the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans.

Suitable dispersing agents are well known in the art, and include but are not limited to surfactants and the like. For example, surfactants that are generally used in the art to reduce surface induced aggregation of ketamine caused by atomization of the solution forming the liquid aerosol may be used. Non-limiting examples of such surfactants are surfactants such as polyoxyethylene fatty acid esters and alcohols, and polyoxyethylene sorbitan fatty acid esters. Amounts of surfactants used will vary, being generally within the range or 0.001 and 4% by weight of the formulation. Suitable surfactants are well known in the art, and can be selected on the basis of desired properties, depending on the specific formulation, concentration of ketamine, diluent (in a liquid formulation) or form of powder (in a dry powder formulation), etc.

The liquid aerosol formulations contain ketamine and a dispersing agent in a physiologically acceptable diluent. The dry powder aerosol formulations of the present invention consist of a finely divided solid form of ketamine and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

In a particular embodiment, the mass median dynamic diameter will be 5 micrometers or less in order to ensure that the drug particles reach the lung alveoli (Wearley, L. L., 1991, 1991, Crit. Rev. in Ther. Drug Carrier Systems 8: 333).

With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

As noted above, in a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art. In a preferred aspect, particularly for treatment of substance addiction, the metered inhaler contains a lock-out mechanism to limit the frequency of administration of doses of ketamine. Such a device is envisioned as an electronic externally programmable or changeable switch for different settings, or a hydraulic or pressure system that requires some time to recharge.

For nasal administration, a useful device is a small, hard bottle to which a metered dose sprayer is attached. In one embodiment, the metered dose is delivered by drawing the ketamine solution into a chamber of defined volume, which chamber has an aperture dimensioned to aerosolize the aerosol formulation by forming a spray when a liquid in the chamber is compressed. The chamber is compressed to administer the ketamine. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Often, the aerosolization of a liquid or a dry powder formulation for inhalation into the lung will require a propellent. The propellent may be any propellant generally used in the art. Specific non-limiting examples of such useful propellants are a chloroflourocarbon, a hydrofluorocarbon, a hydochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., Aerosols and the Lung, Clarke, S. W. and Davia, D. editors, pp 197-22 and can be used in connection with the present invention.

In a further embodiment, as discussed in detail infra, an aerosol formulation of the present invention can include other therapeutically or pharmacologically active ingredients in addition to ketamine, such as but not limited to a benzodiazepine or a narcotic analgesic.

In general, as described in detail infra, ketamine is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of ketamine in an aerosol formulation of the invention.

Liquid Aerosol Formulations

The present invention provides aerosol formulations and dosage forms for use in treating subjects suffering from pain. In general such dosage forms contain ketamine in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactants and excipients.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising ketamine and another therapeutically effective drug, such as a benzodiazepine or a narcotic analgesic.

Aerosol Dry Powder Formulations

It is also contemplated that the present aerosol formulation can be prepared as a dry powder formulation comprising a finely divided powder form of ketamine and a dispersant.

In another embodiment, the dry powder formulation can comprise a finely divided dry powder containing ketamine, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising ketamine and another therapeutically effective drug, such as a benzodiazepine or a narcotic analgesic.

Administration Via Suppositories

In another aspect, ketamine is formulated in a matrix suitable for rectal (or vaginal) insertion, i.e., in a suppository. The invention is not limited to any particular suppository formulation. Indeed, many suppository formulations are known in the art, e.g, as described in *Reminton's Pharmaceutical Sciences, Physician's Desk Reference,* and *U.S. Pharmacopeia.*

Administration via suppositories may be preferred in certain situations, e.g., because convention and custom prefers it, or where nasal administration is deemed unacceptable.

Administration Via a Buccal Patch

According to the invention, ketamine can be formulated in a buccal patch for administration via the interior of the cheek. It may be appreciated that a buccal patch constitutes another form of transmucosal administration. The technology for preparing buccal patch formulations is known in the art, e.g., *Remington's Pharmaceutical Sciences,* supra.

Sublingual and Oral Pharyngal Administration

In yet another embodiment, ketamine can be formulated for sublingual and/or oral pharyngeal, including transbuccal, administration. For example, ketamine can be incorporated in a "candy" matrix, such as that described in U.S. Pat. No. 4,671,953, in a gum base, or a lozenge. In another embodiment, the ketamine can be formulated in a capsule or pill form for sublingual placement.

It is contemplated that sublingual or oral pharyngeal administration may be desirable in connection with treatment for smoking cessation. The formulation for delivery is via the mouth may, in addition to the effects mediated by ketamine, also satisfy the desire of a smoker or other tobacco user for oral fixation. In this respect, a chewing gum may be particularly preferred.

Other Routes of Administration

As noted above, the present invention is not limited to any particular mode or route of administration of ketamine. Accordingly, where medical necessity or preference dictates, parenteral administration of ketamine can be effected for detoxification and treatment for addiction. In particular, for severe cases of withdrawal accompanied by delirium tremens and other violent physical symptoms, intramuscular of intravenous ketamine may be preferred.

The invention further contemplated long term sustained dose administration of ketamine, e.g., via a transdermal patch, osmotic pumps, polymer matrix, or other known means for long term sustained administration of a drug.

Additional Therapeutically Active Drugs or Agents

As note above, the invention contemplates coordinate administration of ketamine with a therapeutically effective amount of another drug, in particular a benzodiazepine or a narcotic analgesic.

Co-administration of ketamine with a benzodiazepine is indicated to counteract the potential dysphoric or hallucinogenic effects of high dose administration of ketamine. Thus, a therapeutically effective amount of a benzodiazepine is an amount effective to inhibit dysphoria. In a further embodiment, an amount of a benzodiazepine also effective to sedate the patient may be administered.

The mild adverse effects of ketamine, e.g., dysphoria and/or hallucinations, sometimes called "ketamine dreams," can occur upon administration of a dose of greater than 50 mg of ketamine, and usually require doses greater than 100 mg of ketamine. One advantage of the present invention is that the effective dose of ketamine is a level effective for analgesia, but below the level that results in dysphoria. However, it is possible that an individual may overdose, particularly in response to an acute episode. Thus, co-administration of a benzodiazepine may be indicated in certain circumstances.

Benzodiazepines that may be administered according to the present invention include, but are not limited to, flurazepam (Dalmane), diazepam (Valium), and preferably, Versed. In a preferred aspect, the transmucosal formulation of the invention comprises ketamine and a benzodiazepine, each present in a therapeutically effective amount.

The invention can be better understood by referring to the following example, which is provided merely by way of exemplification and is not intended to limit the invention.

EXAMPLE

The following is a case report concerning K. N., a male approximately 40 years old, and L. O., a female approximately 40 years old. Both patients, who were married to each other, were smoking 1–3 packs of cigarettes daily for at least ten years. None of the conventional treatments for smoking cessation succeeded with this couple. Otherwise, both subjects were in good health, with no history of illness. After interview they were titrated on nasal spray ketamine. K. N. claimed not to be addicted to cigarettes, but to only smoke when his wife lit up. On questioning, she admitted strong addiction with withdrawal phenomenon.

A short period (1–2 hours) without a cigarette was requested. A lit cigarette and a can of beer were presented in the milieu of a social situation to the couple. L. O. admitted a strong desire to smoke. K. N. had no such craving but said he could smoke if she did. Five mg. of nasal ketamine was administered to L. O. Within 30 seconds she had no desire to light up. She was given the remaining drug in the spray bottle and told to take the same dose (one puff) in the event of a future craving for cigarettes.

Follow-up phone contact at five days indicated no problem except for some irritability. Neither patient experienced extreme difficulty with avoiding smoking, and neither reported smoking or use of any tobacco products, drugs, or alcohol.

Follow-up over weeks and several months indicated that the couple was tobacco free. L. O. was told to use the 50 doses (5 ml containing 250 mg ketamine, 0.1 ml per dose) of ketamine she was given on the first and only meeting with the physician. She had some desire to smoke after the 5 days of acute withdrawal, but administration of a nasal dose of ketamine overcame this urge. She has not asked to renew the medication. The patient reported no smoking or substitute addictions, and no weight gain To date, dozens of patients, including subjects suffering from intractable pain, severe migraine headaches, chronic fatigue syndrome, and other painful afflictions, have successfully employed nasal administration of ketamine to treat these problems. Furthermore, those patients who started treatment as smokers, and who desired to quit smoking, have found that nasal ketamine strongly suppresses the urge to smoke. In total, patients have taken over 100,000 doses of nasal ketamine, without any significant problems.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for facilitating detoxification and treating substance addiction in a subject believed to be suffering from substance addiction comprising administering a dose of ketamine effective to facilitate detoxification or treat substance addiction and a benzodiazepine in an amount effective to inhibit dysphoria.

2. The method according to claim 1, wherein the dose of ketamine is approximately 0.01 to approximately 1 mg/kg of body weight.

3. The method according to claim 2, wherein the dose of ketamine is approximately 0.05 to approximately 0.7 mg/kg of body weight.

4. The method according to claim 1, wherein the substance addiction is smoking.

5. The method according to claim 1 wherein the ketamine is administered via a transmucosal route.

6. The method according to claim 1 wherein the transmucosal route is selected from the group consisting of nasal, oral pharyngeal, buccal, sublingual, rectal, and vaginal.

7. The method according to claim 1 wherein the ketamine is administered via a parenteral route.

8. The method according to claim 7 wherein the parenteral route is selected from the group consisting of intravenous and intramuscular.

9. A pharmaceutical composition comprising a dose of about 0.01 mg/kg of body weight to about 1 mg/kg of ketamine in a pharmaceutically acceptable gum.

10. A pharmaceutical composition comprising a dose of about 0.01 mg/kg of body weight to about 1 mg/kg of ketamine in a pharmaceutically acceptable candy.

11. The composition of claim 9, wherein the dose of ketamine is about 0.05 mg/kg to about 0.7 mg/kg.

12. The composition of claim 9, wherein the dose of ketamine is about 1 mg to about 30 mg.

13. The composition of claim 10, wherein the dose of ketamine is about 0.05 mg/kg to about 0.7 mg/kg.

14. The composition of claim 10, wherein the dose of ketamine is about 1 mg to about 30 mg.

* * * * *